United States Patent [19]
Radlowski et al.

[11] Patent Number: 5,210,060
[45] Date of Patent: May 11, 1993

[54] CATALYST FOR CONVERTING SYNTHESIS GAS TO PARAFFIN WAX

[75] Inventors: Cecelia A. Radlowski, Riverside; Mark P. Kaminsky, Winfield, both of Ill.

[73] Assignee: Amoco Corporation, Chicago, Ill.

[21] Appl. No.: 890,445

[22] Filed: May 28, 1992

Related U.S. Application Data

[62] Division of Ser. No. 737,476, Jul. 30, 1991, Pat. No. 5,135,958.

[51] Int. Cl.$^5$ .................. B01J 21/02; B01J 23/02; B01J 23/36
[52] U.S. Cl. .................................................... 502/202
[58] Field of Search ........................................ 502/202

[56] References Cited

U.S. PATENT DOCUMENTS

| | | | |
|---|---|---|---|
| 3,389,965 | 6/1968 | DeRuiter et al. | 23/212 |
| 3,856,702 | 12/1974 | McArthur | 252/432 |
| 3,856,705 | 12/1974 | McArthur | 518/728 |
| 4,024,171 | 5/1977 | McArthur | 260/449.6 M |
| 4,151,190 | 4/1979 | Murchison et al. | 260/449 R |
| 4,199,522 | 4/1980 | Murchison et al. | 260/449 R |
| 4,749,724 | 6/1988 | Quarderer et al. | 518/714 |
| 4,752,623 | 6/1988 | Stevens et al. | 518/714 |
| 4,775,696 | 10/1988 | Prada-Silva et al. | 518/714 |
| 4,801,573 | 1/1989 | Eri et al. | 502/302 |
| 4,831,060 | 5/1989 | Stevens et al. | 518/714 |
| 4,880,763 | 11/1989 | Eri et al. | 502/302 |

OTHER PUBLICATIONS

Dalla Betta et al., Journal of Catalysis, vol. 40, pp. 173-183 (1975).
Anderson, R. B., "The Fischer-Tropsch Synthesis", Chapter 4 (pp. 100-173), Academic Press, New York (1984).
Anderson, R. B., "The Fischer-Tropsch Synthesis", Chapter 6 (pp. 229-264), Academic Press, New York (1984).

Primary Examiner—W. J. Shine
Attorney, Agent, or Firm—Scott P. McDonald; Wallace L. Oliver; Frank J. Sroka

[57] ABSTRACT

A process for converting synthesis gas to paraffin wax by conversion over a partially sulfided rhenium-aluminum borate catalyst containing an alkali metal or alkaline earth metal compound is disclosed. The inventive process and catalyst provide highly efficient and selective conversion of synthesis gas to paraffin wax.

20 Claims, No Drawings

CATALYST FOR CONVERTING SYNTHESIS GAS TO PARAFFIN WAX

This is a divisional of application Ser. No. 07/737,476, filed Jul. 30, 1991, now U.S. Pat. No. 5,135,958.

BACKGROUND OF THE INVENTION

1. Field of the Invention

The invention relates to the conversion of synthesis gas to hydrocarbons and, more particularly, the invention relates to a catalyst and process for converting synthesis gas to paraffin wax.

2. Description of Related Technology

As is well known in the art, synthesis gas ("syngas") is a mixture of carbon monoxide and molecular hydrogen, generally having a hydrogen to carbon monoxide molar ratio in the range of about 1:5 to about 5:1, which may contain substantial amounts of other gases, such as carbon dioxide, for example. Synthesis gas may be prepared by conversion of natural gas, and in turn may be converted to a variety of useful products.

Synthesis gas has utility as a feedstock for conversion to alcohols, olefins, or saturated hydrocarbons (paraffins) according to the well-known Fischer-Tropsch process, and by other means.

One potential use for synthesis gas is as a feedstock for conversion to high molecular weight (e.g. $C_{20}+$, and preferably $C_{50}+$) paraffins which provide an ideal feedstock for hydrocracking for conversion to high quality jet fuel and superior high cetane value diesel fuel blending components.

Paraffins having 15 or more carbon atoms per molecule form wax at ambient conditions and therefore may readily be stored or transported from remote sites of natural gas reserves where syngas may be generated on site and then converted to paraffins.

In addition to the hydrocracking products referred to above, paraffin wax can be cracked to form linear olefins. Linear α-olefins can be reacted with additional syngas over an oxo catalyst in the well known oxo process to produce $C_6$-$C_{10}$ plasticizer alcohols or $C_9$-$C_{13}$ detergent alcohols, both of which are valuable.

SUMMARY OF THE INVENTION

The invention provides a catalyst and process for converting synthesis gas comprising carbon monoxide and hydrogen to paraffin wax which may in turn be converted to useful products.

According to the invention, synthesis gas is contacted under conversion conditions with a partially sulfided, alkali or alkaline earth metal-containing rhenium aluminum borate catalyst.

The invention provides high syngas conversion activity with high selectivity for paraffin wax production.

Further objects and advantages of the invention will be apparent to those skilled in the art from the following detailed description, taken in conjunction with the appended claims.

DETAILED DESCRIPTION OF THE INVENTION

According to the invention, a catalyst precursor comprising a porous aluminum borate (boric oxide, $B_2O_3$) matrix containing rhenium and a compound of an alkali metal or alkaline earth metal is prepared, and partially sulfided by contact with a sulfiding compound to produce a catalyst which is active for efficient synthesis gas conversion and highly selective for the production of high molecular weight (i.e. $C_{20}+$, and preferably $C_{50}+$) paraffins. In a preferred embodiment, the catalyst is partially coked, preferably by reaction of carbon monoxide contained in synthesis gas prior to sulfiding.

More particularly, the catalyst precursor has the nominal composition $ReO_xaAl_2O_3bB_2O_3$ wherein x preferably is about 2 to about 3.5, a is preferably about 3 to about 6, b is preferably about 1 to about 4, and contains about 5 to about 15 wt.% (based on the total catalyst weight) of a compound of an alkali metal or alkaline earth metal. In a highly preferred form, x is about 3, a is about 3.6, b is about 4, and the catalyst precursor contains about 10 wt.% $K_2CO_3$.

The foregoing preferred nominal composition represents a catalyst precursor that nonquantitatively comprises $ReO_3$ and $Al_4B_2O_9$ in crystalline form, and may conveniently be prepared from a perrhenic acid ($HReO_4$) precursor by sol gel techniques, as shown in the Example, below.

According to the preferred sol gel preparation technique, a cogelled alkali or alkaline earth metal-containing rhenium aluminum borate catalyst precursor may be prepared by forming an aqueous solution of suitable sources of oxidized rhenium, boria (e.g. perrhenic acid ($HReO_4$) and boric acid, respectively) and alumina, and adding a compound of an alkali metal or alkaline earth metal in a sufficient amount to raise the pH of the solution to a gel point whereupon cogelation or thickening of a sol gel occurs.

This sol gel preparation technique produces a well integrated catalytic structure characterized by favorable physical properties, which is distinguishable from prior catalysts utilizing aluminum borate supports for catalytic metals.

The catalyst may comprise, and preferably consists or consists essentially of constituents selected from oxidized rhenium, elemental rhenium (under the reducing conditions of the conversion process), oxides of aluminum and boron, sorbed or reacted sulfur, one or more compounds of an alkali metal or alkaline earth metal, and optionally carbon deposited on the catalyst surface by partial coking.

The inventive catalyst may be prepared and used in the absence of any component or step which is not specifically disclosed herein. Additional catalytic metals are neither necessary nor desired i.e., the catalyst is preferably at least substantially free of catalytically active metals other than rhenium, meaning that the catalyst may contain amounts of other materials, including catalytically active materials such as iron, manganese or cobalt in small amounts i.e. less than about 1 wt.%, preferably less than 0.5 wt.%) which are insufficient to affect the nature and level of the catalytic activity of the partially sulfided rhenium aluminum borate catalyst.

The rhenium aluminum borate matrix is generally characterized as having high surface area, preferably in the range of about 5 $m^2/g$ to about 200 $m^2/g$ and typically less than about 130 $m^2/g$ (e.g., about 13 $m^2/g$), and a pore structure characterized as having a predominance of, and preferably consisting or consisting essentially of mesopores, i.e. pores having diameters in the range of about 100 to about 500 Angstroms. A typical precursor pore volume will be in the range of about 0.05 cc/g to about 0.5 cc/g, typically about 0.08 to about 0.09 cc/g, and the catalyst precursor matrix preferably has no or only negligible micropore volume, i.e. pore volume attributable to pores having diameters of less than about 100 Angstroms, and no or only negligible pore volume attributable to pores having diameters greater than 500 Angstroms.

The catalyst precursor is partially sulfided and, optionally, subjected to a partial coking treatment before use as a syngas conversion catalyst.

Sulfiding is preferably carried out by contacting the catalyst precursor with a sulfiding compound under conditions selected to avoid complete sulfiding and total deactivation of the rhenium contained in the catalyst precursor. Partial sulfiding of the rhenium catalyst precursor inevitably results in partial deactivation, and the selectivity of the catalyst for high molecular weight products is believed to reach a maximum when only major, relatively active sites of the rhenium present in the catalyst precursor are sulfided. Further sulfiding is not believed to reduce the selectivity of the catalyst for high molecular weight paraffins, but reduces the activity of the catalyst.

It is believed that optimum selectivity for paraffin wax is attained when the catalyst is sulfided only sufficiently to reduce its activity (compared to an otherwise identical unsulfided catalyst) by about 20 to about 25%, although the catalyst will be selective for paraffin wax if sulfided sufficiently to reduce its activity by up to about 35%.

The sulfiding compound may be gaseous (e.g. $H_2S$) or in liquid form, such as a liquid solution of a sulfiding compound, such as ammonium sulfide or a sulfide of an alkali metal, such as sodium sulfide, for example. In the case of liquid sulfiding solutions, aqueous solutions are preferred for ease of solvent removal from the catalyst precursor which has been impregnated with the solution.

It is preferred to partially sulfide the catalyst precursor by contact with a gaseous sulfiding compound, preferably contained in a gas stream consisting or consisting essentially of a reducing gas such as $H_2$ and a small amount (e.g. about 1 vol.% or less) of $H_2S$. This step is preferably carried out at relatively low temperature and pressure compared with the syngas conversion conditions.

It is preferred to sulfide the catalyst precursor, which optionally may be partially coked before or after sulfiding, using a gaseous sulfiding compound of the type described above at a temperature in the range of about 150° F to about 500° F. and a pressure below about 300 psig. Highly preferably, the gas stream consists essentially of $H_2$ and about 0.2 vol.% $H_2S$ and the sulfiding step is carried out at a pressure of about 100 psig (which is a low pressure selected for ease of flow through the catalyst bed) and a temperature of about 250° F.

The pressure is not critical and the sulfiding step may be carried out at atmospheric pressure or very slightly above in order to promote flow.

The sulfiding temperature when using a gaseous sulfiding compound is selected to be sufficiently low to avoid sintering. The sulfiding reaction is quite rapid, and only a low residence time (e.g. less than several minutes) is needed.

When utilizing a liquid solution of a sulfiding compound, the catalyst precursor, which optionally may be partially coked before or after sulfiding, is impregnated with the solution followed by drying to remove solvent, which is preferably water. The drying conditions are not critical, but a temperature sufficiently low to avoid catalyst sintering is necessary. For example, drying may be effected by heating to 100° C. for at least 4 hours.

The catalyst precursor may be subjected to a partial coking step whereby carbon is deposited on the precursor, before or after but preferably prior to contacting the precursor with the sulfiding compound. The function of the coking step is to partially cover the catalyst precursor surface with carbon in order to passivate active catalyst sites which are not selective for paraffin wax production.

A convenient means of carrying out the partial coking step is to contact the precursor with synthesis gas at a temperature at which carbon monoxide reacts to produce carbon, probably by the Bouduard carbon monoxide disproportionation reaction or by a secondary hydrocarbon reaction whereby carbon monoxide reacts with hydrogen to form hydrocarbons which in turn adsorb on the catalyst surface in the form of coke. Such reactions generally occur at temperatures in the range of about 390° F. to about 1115° F., and are carried out for a time period (generally less than one week and preferably more than 48 hours, typically 3 to 4 days) sufficient to cover a portion of the precursor surface with carbon. The reaction may be carried out at any convenient pressure and preferably at an elevated pressure, e.g. about 2000 psig.

Preferably, the partial coking reaction is carried out at a temperature of about 600° F. and a pressure of about 2000 psig for at least about 48 hours.

In practice, the catalyst precursor may be converted to the catalyst by treatment in situ in the syngas conversion reactor by, for example, (a) optionally partially coking the catalyst by flowing synthesis gas over the catalyst at an elevated temperature and pressure for a sufficient time period to effect partial coking; (b) thereafter reducing the temperature and pressure and introducing a flow of reducing gas containing $H_2S$ in order to partially sulfide the catalyst precursor, followed by (c) flushing the $H_2S$ from the reactor with synthesis gas and (d) setting an appropriate reaction temperature and pressure for syngas conversion. Conversion is generally carried out at a temperature of at least about 400° F. and at a pressure of at least about 500 psig, preferably at a temperature in the range of about 500° F. to about 800° F. and at a pressure of about 1000 psig to about 2000 psig.

In the past, it was believed that sulfur severely poisons rhenium as a Fischer-Tropsch synthesis gas conversion catalyst. According to the invention, however, little syngas conversion activity is lost due to partial sulfiding. For example, a typical rhenium catalyst made according to the invention but without sulfiding converts more than 80% of carbon monoxide present in a synthesis gas feed. After the partial sulfiding treatment of the invention, the catalyst typically is still capable of converting more than 60% of the carbon monoxide in the feed.

Hydrogen sulfide and other sulfiding compounds chemisorb on the surface of the aluminum borate rhenium catalyst precursor of the invention. At complete coverage, sulfur completely blocks the active rhenium surface, which severely limits the number of carbon monoxide molecules which can adsorb on the surface, hence limiting the attainable degree of conversion of carbon monoxide. Such complete coverage of the surface by sulfur results in total or nearly total deactivation of the catalyst.

Sulfur compounds, on being adsorbed, decrease the electron density of metals. This tendency would in principal disfavor carbon monoxide adsorption, weaken the carbon-metal bond and strengthen the carbon-oxygen bond. The net result would be expected to be a decrease in the formation of high molecular weight products. However, according to the invention, efficient high yield production of high molecular weight paraffins is possible after partial sulfiding of the catalyst. Therefore, although the inventors do not wish to be bound by this theory, it appears that the effect of sulfur compounds in promoting the production of high molecular weight paraffins is probably not related to the electron withdrawing tendency of such compounds.

It is postulated that the catalytic surface consists of active rhenium sites of varying size and activity, and that the major, more active sites produce relatively low molecular weight products. It is theorized that sulfur preferentially adsorbs on these more active sites, thus favoring the production of higher molecular weight products.

Thus, according to the invention, the catalyst is preferably prepared in such a way as to sulfide all or most of the relatively active major rhenium sites in order to favor the production of high molecular weight products (i.e. to promote the selectivity of the catalyst for high molecular weight paraffin products) while maintaining an acceptably high activity level.

EXAMPLE

The practice of the invention will be illustrated by reference to the following specific example, but the scope of the invention is not to be limited thereby.

Preparation of Catalyst Precursor

A catalyst precursor designated Catalyst A and having the nominal composition $ReO_3 3.6Al_2O_3 4B_2O_3$ with 10 wt.% $K_2CO_3$ was prepared as follows using sol gel techniques.

Boric acid (14.39 gm, 0.233 mole) was added to 0.06 L of distilled water and heated to dissolve. An aqueous solution of 85% perrhenic acid (10 gm, 0.03 mole $HReO_4$) was then added to the boric acid solution and stirred for several minutes. This solution was added to PHF alumina sol from American Cyanamid Co. (11% solids, 108 gm) and stirred in a Waring blender while heating to 55° C. (131° F.). The resulting solution was stirred for 15 minutes at a pH of 3. A $K_2CO_3$ solution (2.55 gm, 0.0185 mole in 5 mL $H_2O$) was added dropwise to the solution, causing it to thicken. Gel thickening was complete at a pH of 11. The gel was then air dried on a tray for 24 hours before pretreating to 400° C. (752° F.) in air for two hours. Calcination was done at 600° C. (1112° F.) for eight hours.

Nitrogen BET analysis of the calcined material indicated a surface area of 13 $m^2$/gm and a mesopore volume of 0.0864 cc/gm.

X-ray diffraction analysis showed that after calcination the material contained $ReO_3$, $Al_4B_2O_9$, and an unidentified phase. The material had only a medium degree (i.e., about 40–60%) of crystallinity.

Thermogravimetric analysis showed that rhenium oxide sublimed out of the material at 700 to 760° C. (1292° to 1400° F.). A sharp exotherm was observed in this temperature range. Elemental analysis of the samples calcined above these temperatures showed that the catalyst was depleted in rhenium.

Metals analysis of the catalyst by inductively coupled plasma techniques showed it contained 18.5 wt.% Re; 8.5 wt.% B; 21.2 wt.% Al; and 5.1 wt.% K on an elemental basis. This indicated the catalyst had not lost rhenium during calcination.

Partial Coking and Sulfiding of Catalyst Precursor

A catalyst designated Catalyst B was prepared from a portion of Catalyst A as follows.

A quantity of Catalyst A particles was ground to 12/20 mesh size and 5 grams (6.4 cc) of ground Catalyst A particles were mixed with 11.6 cc of an activated carbon diluent and charged to a stainless steel tube reactor. The unit was pressured up to 2000 psig with synthesis gas having a nominal composition of 65 vol.% $H_2$/32 vol.% CO/3 vol.% $CO_2$ ($H_2$:CO molar ratio of about 2:1).

The reactor was heated to 600° F. and the catalyst was exposed to the synthesis gas for at least 48 hours. The pressure was then lowered to 100 psig and the temperature was lowered to 250° F. A gas stream containing 2000 ppm $H_2S$ and the balance hydrogen was allowed to flow through the catalyst bed until breakthrough of the hydrogen sulfide was observed at the reactor exit. ($H_2S$ breakthrough may occur in 1 hour or less, depending on the size of reactor and gas flow rate.) H S was then flushed out with $H_2$ and the unit was pressured back up to 2000 psig with synthesis gas of the composition given above.

Synthesis Gas Conversion Tests

Each of the nonsulfided and sulfided Catalysts A and B, respectively, was tested for syngas conversion using synthesis gas of the composition described above at 600° F. and 2000 psig with a GHSV of 1800–1900 cc syngas/hr.-g.cat. Each catalyst was tested for two days.

Baseline conditions were established by passing the synthesis gas feed over the catalyst at the desired pressure and $H_2$:CO molar ratio at room temperature. The volumetric gas effluent rate in cubic feet per hour was measured by a wet test meter over the course of at least 16 hours. An on-line gas sample was analyzed to establish the initial CO and $CO_2$ concentrations. Hydrogen concentration was measured by difference. The reactor temperature was raised over several hours time to the desired reaction temperature. The effluent gas flow rate was measured by a wet test meter after at least 16 hours at reaction temperature. Then on-line and off-line gas samples were analyzed, and the condensable liquids were collected.

The calculations for CO conversion, selectivity, and space time yield were performed as follows:

% CO Conversion =

$$\frac{(GHSV\ inlet)(\%\ CO\ inlet) - (GHSV\ outlet)(\%\ CO\ outlet)}{(GHSV\ inlet)(\%\ CO\ inlet)}$$

% Selectivity =

(% component)(% CO feed/100)(% CO converted/100)

Space Time Yield (g component/hr/kg catalyst) =

(GHSV/22.4)(% CO feed/100)(% CO conv./

100)(% comp. wt. selectivity)(M.W./C no.)

All components were analyzed by three chromatographic systems. The fixed gases (CO, $CO_2$ and $CH_4$)

were analyzed by an on-line Hewlett-Packard 5730 gas chromatograph equipped with a thermal conductivity detector and a Chromosorb 106 packed column. Analysis was accomplished by using an external standard calibrated for CO, $CO_2$ and $CH_4$. The non-condensable light gases ($C_1$–$C_6$) were analyzed off-line using a flame ionization detector and a six-foot n-octane Porosil C column. The peaks were identified by matching retention times with those of a known $C_1$–$C_6$ hydrocarbon calibration mixture. Relative weight percentages of the light gases were obtained this way. The condensable materials were collected in a bomb and analyzed with a flame ionization detector equipped with a 30 meter capillary column of fused silica containing RSL 160 brand liquid phase. Peaks were identified by matching retention times of known alcohols, aldehydes, esters, ketones, olefins, and paraffins. Many of the smaller peaks were not identified. Relative weight percents were obtained.

Conversion results are shown in the following Tables I and II.

TABLE I

| | Catalyst A (Not Sulfided) | |
|---|---|---|
| Day | 1 | 2 |
| Inlet | | |
| GHSV | 1805.5 | 1805.5 |
| % CO | 32.1 | 32.1 |
| % $CO_2$ | 2.9 | 2.9 |
| Outlet | | |
| GHSV | 879.1 | 950.9 |
| % CO | 12.61 | 9.5 |
| % $CO_2$ | 20.6 | 22.4 |
| % $CO_4$ | 17.4 | 18.6 |
| % CO Conversion | 80.9 | 84.5 |
| % Selectivity/Yield | | |
| (g/g cat.-hr.) | | |
| $CO_2$ | 27.4 | 32.7 |
| $CH_4$ | 32.6 | 36.1 |
| $C_2$–$C_3$ hydrocarbons | 12.1 | 14.1 |
| $C_4$+ hydrocarbons | 5.2 | 6.5 |
| MeOH | 4.3 | 2.2 |
| EtOH | 9.2 | 4.4 |
| $C_3$OH | 4.9 | 2.2 |
| $C_4$OH | 2.0 | 0.9 |
| $C_5$+ alcohols, and others | 2.4 | 0.9 |

TABLE II

| | Catalyst B (Sulfided) | |
|---|---|---|
| Day | | 12 |
| Inlet | | |
| GHSV | 1895.0 | 1895.0 |
| % CO | 32.2 | 32.2 |
| % $CO_2$ | 2.9 | 2.9 |
| Outlet | | |
| GHSV | 1127.8 | 1127.8 |
| % CO | 19.8 | 17.3 |
| % $CO_2$ | 13.6 | 15.7 |
| % $CO_4$ | 10.6 | 12.9 |
| % CO Conversion | 63.4 | 69.6 |
| % Selectivity/Yield | | |
| (g/g cat.-hr.) | | |
| $CO_2$ | 25.3 | 26.9 |
| $CH_4$ | 30.9 | 32.7 |
| $C_2$–$C_3$ hydrocarbons | 11.4 | 12.8 |
| $C_4$+ hydrocarbons | 4.3 | 4.9 |
| Waxy hydrocarbons (including very small amounts of $C_1$–$C_5$ alcohols) | 28.1 | 22.7 |

Discussion

At the tested conditions, Catalyst A converted over 80% of the carbon monoxide feed producing a hydrocarbon product comprising mainly methane. The other hydrocarbons present were mainly straight chain paraffins which follow a Schulz-Flory distribution. Very small amounts of branched paraffins, olefins and wax were also observed. The liquid product which was obtained was an aqueous solution containing mostly $C_1$–$C_5$ straight chain, normal alcohols. Ethanol was the most abundant alcohol formed.

After partial coking and $H_2S$ treatment to produce Catalyst B, the catalyst activity declined to about 60–70% CO conversion. The products were mostly waxy hydrocarbons, methane, carbon dioxide, and $C_1$–$C_3$ hydrocarbons. The weight of the waxy hydrocarbons was determined by difference as a complete mass balance was not possible due to plugging of the reactor by wax formation.

The foregoing detailed description is given for clearness of understanding only, and no unnecessary limitations should be understood therefrom, as modifications within the scope of the invention will be apparent to those skilled in the art.

We claim:

1. A catalyst comprising a partially sulfided catalyst precursor which comprises rhenium, porous aluminum borate, and a compound of an alkali metal or alkaline earth metal.

2. The catalyst of claim 1 wherein said catalyst precursor is prepared by cogelation from an aqueous solution of sources of oxidized rhenium, alumina and boria promoted by the addition to said solution of said compound of an alkali metal or alkaline earth metal.

3. The catalyst of claim 1 wherein said catalyst has a specific surface area in the range of about 5 m g to about 200 $m^2$/g and comprises a predominance of pores having diameters in the range of about 100 to about 500 Angstroms.

4. The catalyst of claim 1 wherein said catalyst precursor is of the nominal composition $ReO_x$a$Al_2O_3$b-$B_2O_3$ wherein x is about 2 to about 3.5, a is about 3 to about 6, b is about 1 to about 4, and contains about 5 to about 15 wt.% of said compound of an alkali metal or alkaline earth metal, based on the total catalyst precursor weight.

5. The catalyst of claim 4 wherein said catalyst precursor comprises $ReO_3$ and $Al_4B_2O_9$ in crystalline form and said compound of an alkali metal is $K_2CO_3$.

6. The catalyst of claim 1 wherein said catalyst precursor is partially sulfided by contact with a sulfiding compound under conditions selected to avoid complete sulfiding and total deactivation of the rhenium contained in said catalyst precursor.

7. The catalyst of claim 6 wherein said sulfiding compound is $H_2S$ and said catalyst precursor is contacted with a gas stream comprising said $H_2S$ at a temperature which is sufficiently low to avoid sintering of said aluminum borate.

8. The catalyst of claim 7 wherein said gas stream consists essentially of $H_2$ and about 1 vol.% or less $H_2S$ and said sulfiding is carried out at a temperature in the range of about 150° F. to about 500° F. and a pressure below about 300 psig.

9. The catalyst of claim 6 wherein said catalyst precursor is contacted with said sulfiding compound by impregnation with a liquid solution of said sulfiding compound.

10. The catalyst of claim 9 wherein said sulfiding compound is selected from the group consisting of ammonium sulfide and sulfides of alkali metals.

11. The catalyst of claim 6 wherein said catalyst precursor is subjected to partial coking whereby carbon is deposited on the surface of said catalyst precurosr.

12. The catalyst of claim 1 wherein said partial coking comprises contacting said catalyst precursor with synthesis gas at a carbon monoxide reaction temperature and at a pressure and for a time period sufficient to cover a portion of said catalyst precursor surface with carbon prior to contacting said catalyst precursor with said sulfiding compound.

13. A catalyst comprising a partially sulfided catalyst precursor comprising rhenium, porous aluminum borate, and a compound of an alkali metal, or alkaline earth metal, said catalyst having a specific surface area in the range of about 5 m$^2$/g to about 200 m$^2$/g and being characterized by a pore volume in the range of about 0.05 cc/g to about 0.5 cc/g attributable to pores having diameters in the range of about 100 to 500 Angstroms, said catalyst precursor being of the nominal composition ReO$_x$.$a$Al$_2$O$_3$.$b$B$_2$O$_3$ wherein x is about 2 to about 3.5, a is about 3 to about 6, and b is about 1 to about 4, and containing about 5 to about 15 wt.% of said compound of an alkali metal or alkaline earth metal based on the total catalyst precurosr weight, and said catalyst precurosr being partially sulfided by contact with a sulfiding compound under conditions selected to avoid complete sulfiding and total deactivation of the rhenium contained in said catalyst precursor.

14. The catalyst of claim 13 wherein said catalyst precursor is prepared by cogelation from an aqueous solution of sources of oxidized rhenium, alumina, and boria promoted by the addition to said solution of said compound of an alkali metal or alkaline earth metal.

15. The catalyst of claim 13 wherein said sulfiding compound is H$_2$S and said catalyst precursor is contact with a gas stream comprising H$_2$S at a temperature in the range of about 150° F. to about 500° F. and a pressure below of about 300 psig.

16. The catalyst of claim 13 wherein said catalyst precursor is subjected to partial coking by contacting said catalyst precursor with synthesis gas at carbon monoxide reaction conditions whereby carbon is deposited on the surface of said catalyst precursor prior to contacting said catalyst precursor with said sulfiding compound.

17. A catalyst comprising a partially sulfided catalyst precursor comprising rhenium, porous aluminum borate, and a compound of an alkali metal, or alkaline earth metal, said catalyst having a specific surface area in the range of about 5 m$^2$/g to 200 m$^2$/g and being characterized by a pore volume in the range of about 0.05 cc/g to about 0.5 cc/g attributable to pores having diameters in the range of about 100 to 500 Angstroms, said catalyst precursor being of the nominal composition ReO$_x$.$a$Al$_2$O$_3$.$b$B$_2$O$_3$ wherein x is about 2 to about 3.5, a is about 3 to about 6, and b is about 1 to about 4, and containing about 5 to about 15 wt.% of said compound of an alkali metal or alkaline earth metal based on the total catalyst precursor weight, said catalyst precurosr being prepared by cogelation from an aqueous solution of sources of oxidized rhenium, alumina, and boria promoted by the addition to said solution of said compound of an alkali metal or alkaline earth metal, said catalyst precursor being partially sulfided by contact with a sulfiding compound under conditions selected to avoid complete sulfiding and total deactivation of the rhenium contained in the said catalyst precursor, and said catalyst precursor being subjected to a partial coking step whereby carbon is deposited on the surface of said catalyst precursor prior to contacting said precursor with said sulfiding compound.

18. The catalyst of claim 17 wherein said sulfiding compound is H$_2$S and said catalyst precursor is partially sulfided by being contacted with a gaseous stream consisting essentially of H$_2$ and about 1 vol.% or less of H$_2$S at a temperature in the range of about 150° F. to about 500° F. and a pressure below about 300 psig.

19. The catalyst of claim 17 wherein said catalyst precursor is partially sulfided by being contacted with a sulfiding compound selected from the group consisting of ammonium sulfide and sulfides of alkali metals by impregnation with a liquid solution of said sulfiding compound.

20. The catalyst of claim 17 wherein said partial coking comprises contacting said catalyst precursor with synthesis gas at carbon monoxide reaction conditions for a time period sufficient to cover a portion of said catalyst precursor surface with carbon.

* * * * *